US006443888B1

(12) United States Patent
Ogura et al.

(10) Patent No.: US 6,443,888 B1
(45) Date of Patent: Sep. 3, 2002

(54) ENDOSCOPE HAVING ELECTRICAL CONTACT FOR CONNECTING TO CONTROL UNIT A FORMED IN CONNECTOR UNIT

(75) Inventors: Takeshi Ogura; Haruhiko Kaiya, both of Hachioji; Takahiro Kishi, Yokohama, all of (JP)

(73) Assignee: Olympus Optical Co. Ltd. (JP)

( * ) Notice: Subject to any disclaimer, the term of this patent is extended or adjusted under 35 U.S.C. 154(b) by 0 days.

(21) Appl. No.: 09/369,002

(22) Filed: Aug. 5, 1999

(30) Foreign Application Priority Data

Aug. 6, 1998 (JP) ............................................. 10-223254

(51) Int. Cl.$^7$ ................................................. A61B 1/04
(52) U.S. Cl. ........................................................ 600/132
(58) Field of Search ................................ 600/132, 110, 600/133; 348/75

(56) References Cited

U.S. PATENT DOCUMENTS 4,667,655 A * 5/1987 Ogiu et al. .................. 600/132
4,888,639 A * 12/1989 Yabe et al. .................. 600/132
5,159,446 A * 10/1992 Hibino et al. ............... 600/152

FOREIGN PATENT DOCUMENTS

JP 3-178630 8/1991

* cited by examiner

Primary Examiner—John Mulcahy
(74) Attorney, Agent, or Firm—Ostrolenk, Faber, Gerb & Soffen, LLP

(57) ABSTRACT

An endoscope system includes an endoscope, two control apparatuses, electric cables, and two electric connector receptacles. The endoscope has a connector unit, which includes a light source connector to be coupled to a light source apparatus, fixed to the proximal end of a universal cord extending from an operation unit. The two control apparatuses electrically control the endoscope. The electric cables electrically link the control apparatuses and the endoscope. The two electric connector receptacles are included in the connector unit of the endoscope. Connectors attached to the electric cables are coupled to the two electric connector receptacles. When the connector of one of the electric cables is mounted on a first electric connector receptacle of the two electric connector receptacles, the direction in which the connector is oriented to be mounted is orthogonal to the direction in which the light source connector is oriented to be coupled to the light source apparatus. When the connector of the other electric cable is mounted on a second electric connector receptacle, the direction in which the connector is oriented to be mounted is the same as the direction in which the light source connector is oriented to be coupled to the light source apparatus.

6 Claims, 6 Drawing Sheets

FIG.1

ENDOSCOPE SYSTEM

ENDOSCOPE HAVING ELECTRICAL CONTACT FOR CONNECTING TO CONTROL UNIT A FORMED IN CONNECTOR UNIT

BACKGROUND OF THE INVENTION

1. Field of the Invention

The present invention relates to an endoscope system including an endoscope and a control apparatus for electrically controlling the endoscope.

2. Description of the Related Art

Endoscopes for observing internal organs and for various kinds of medical treatment are widely used. During observation of internal organs, an elongated insertion unit of the endoscope is inserted into a body cavity. The endoscope for various kinds of cures or treatments is used with a treatment appliance inserted into a treatment appliance channel lying through the endoscope.

Endoscopes fall into two types: optical and electronic. The optical endoscope transmits a view over an image guide to an eyepiece unit for observation. The electronic endoscope has a solid-state imaging device, such as a charge-coupled device (hereinafter, CCD), included as an imaging means in the distal part of the insertion unit. In the electronic endoscope, an optical image is formed on the CCD via an objective optical system and photoelectrically converted into an image signal. Based on the image signal, a video processor produces a video signal. An endoscopic image is then displayed on a monitor screen for observation.

The endoscope may include a bending mechanism for electrically controlling bending of a bendable part. Moreover, since the electronic endoscope includes the CCD in the distal part of the insertion unit, a plurality of signal cables passes through the endoscope.

The signal cables are contained in a universal cord extending from one side of an operation unit of the endoscope. The signal cables are spliced to an electrical connector formed on one side of a light source connector attached to the proximal end of the universal cord. The electrical connector and an external control apparatus are linked by an electric cable. A driving current is supplied or signals are transferred over the electric cable.

A typical endoscope is designed to be held with the left hand. The electric cable is therefore coupled or uncoupled with the right hand. The electric connector is therefore located on the right-hand side of the light source connector with the light source connector opposed to a light source apparatus.

In addition to the signal cables, a light guide reaching the light source connector, an aeration tube, a perfusion tube or suction tube, and a pressurization tube are pass through the endoscope. A suction base and contacts for aeration, perfusion, and pressurization, via which the tubes are connected to external apparatuses, such as an aeration pump, perfusion pump, and suction pump, are formed on the sides of the light source connector.

The plurality of tubes and electric cables juts out of the side of the light source connector in a direction orthogonal to the direction in which the light source connector is inserted into the light source apparatus. Consequently, the surroundings of the light source connector are congested and deteriorate the smoothness in coupling the electric cables and tubes.

A solution to this problem, a relay cord coupled to an AWS unit and a relay cord coupled to the control apparatus are coupled to the sides of a light source connector in an endoscope system, as disclosed in Japanese Unexamined Patent Publication No. 3-178630. The AWS unit controls aeration, perfusion, and suction.

However, as described in the Japanese Unexamined Patent Publication No. 3-178630, when two relay cords are coupled to the sides of the light source connector, one of the relay cords must be coupled using the right hand in a backhand manner, which deteriorates smoothness in coupling.

A technology for extending novel control electrically in addition to conventional electric control of an endoscope has been developed. An electric connector must therefore be formed to connect a control apparatus for extending the novel control to the endoscope. If the new electric connector is oriented in a direction opposite to the direction in which a conventional electric connector is oriented, the smoothness in coupling an electric cable to the new electric connector is degraded. The surroundings of the connector also are congested.

SUMMARY OF THE INVENTION

An object of the present invention is to provide an endoscope system offering improved smoothness in coupling electric cables and tubes.

Another object of the present invention is to provide an endoscope system having coupled electric cables and tubes neatly arranged near a connector.

Briefly, according to the present invention, there is provided an endoscope system including an endoscope, two control apparatuses, electric cables, and two electric connector receptacles. The endoscope has a connector unit, which includes a light source connector to be coupled to a light source apparatus, fixed to the proximal end of a universal cord extending from an operation unit. The two control apparatuses electrically control the endoscope. The electric cables link the control apparatuses and the endoscope. The two electric connector receptacles are formed in the connector unit of the endoscope to which connectors attached to the electric cables are coupled.

When the connector of one electric cable is received on a first electric connector receptacle, the direction in which the connector is oriented is orthogonal to the direction in which the light source connector is oriented to be coupled to the light source apparatus. When the connector of the other electric cable is received on a second electric connector receptacle, the direction in which the connector is oriented is the same as the direction in which the light source connector is oriented to be coupled to the light source apparatus. The first electric connector receptacle and second electric connector receptacle a re located on the right-hand side of the connector unit with the connector unit opposed to the light source apparatus.

The invention is described below with reference to the following figures, throughout which similar reference characters denote corresponding features consistently, wherein.

DESCRIPTION OF THE PREFERRED EMBODIMENTS

An embodiment of the present invention will be described with reference to FIG. 1 to FIG. 10.

Figure 1:
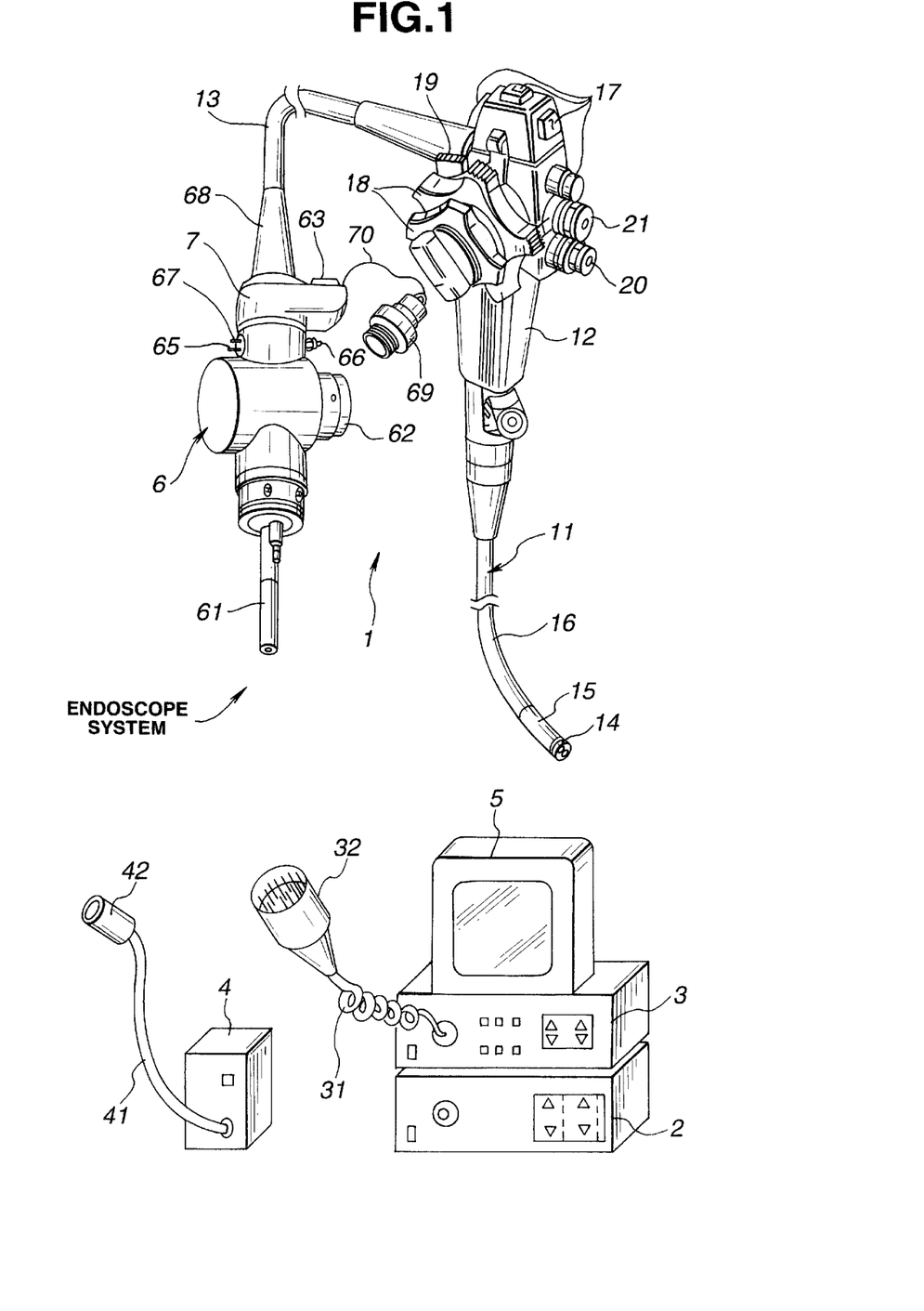
FIG. 1 is perspective view of an endoscope system having an endoscope and a control apparatus constructed according to principles of the invention.

As shown in FIG. 1, an endoscope system in accordance with the present embodiment consists mainly of an electronic endoscope (hereinafter, endoscope) 1, a light source apparatus 2, a video processor 3, and a magnification control apparatus 4. The endoscope 1 has a solid-state imaging device, (not shown) incorporated in an insertion unit 11 thereof. The light source apparatus 2 supplies light to the endoscope 1 for observation. The video processor 3 is a first control apparatus for driving the solid-state imaging device of the endoscope 1 and processing signals output from the solid-state imaging device. The magnification control apparatus 4 is a second control apparatus for electronically controlling the magnifications to be provided by an observation optical system (not shown) incorporated in the distal part of the endoscope 1. Thus, observation of a magnified view is enabled.

Connected to the video processor 3 over a video cable (not shown) is, for example, a liquid-crystal monitor 5. A view produced by the electronic endoscope 1 is displayed on the screen of the liquid-crystal monitor 5 by way of the video processor 3. The second control apparatus may be, aside from the magnification control apparatus 4, a control apparatus for detecting or controlling the bent shape of a bendable part, a control apparatus for detecting or controlling the shape of the insertion unit 11, or a control apparatus for controlling stereoscopic display. These control apparatuses can be connected depending on the application.

The endoscope 1 consists of the insertion unit 11, an operation unit 12, and a universal cord 13. The insertion unit 11 is elongated and has, for example, plasticity. The operation unit 12 communicates with the proximal end of the insertion unit 11. The universal cord 13 extends from one side of the operation unit 12, has plasticity, and has a plurality of signal cables, a light guide, and various tubes therein.

The insertion unit 11 has a rigid distal part 14 connected to a bendable part 15 connected to a flexible tube 16. The rigid distal part 14 has the solid-state imaging device incorporated therein. The bendable part 15 has a plurality of jointed bendable pieces, and can bend freely in vertical and lateral directions. The flexible tube 16 has plasticity.

Arranged on the operation unit 12 are a switch unit 17, a bending knob 18, a zoom switch 19, an aeration/perfusion button 20, and a suction button 21. The switch unit 17 is used to freeze a view appearing on the screen of the liquid-crystal monitor 5, remotely control the video processor 3, and remotely adjust an amount of light emanating from the light source apparatus 2. The bending knob 18 is used to bend the bendable part 15. The zoom switch 19 is used to change the magnification to vary the image magnification. The aeration/perfusion button 20 is used to control aeration or perfusion and the suction button 21 is used to control suction.

A connector unit 6 is fixed to the proximal end of the universal cord 13.

Figure 2:
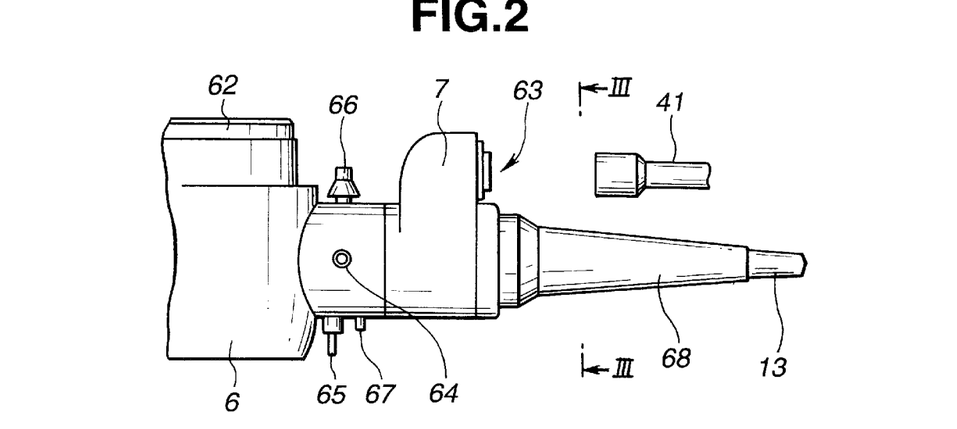
FIG. 2 is a side elevational view for explaining a magnification-control connector unit of the embodiment of FIG. 1.
Figure 3:
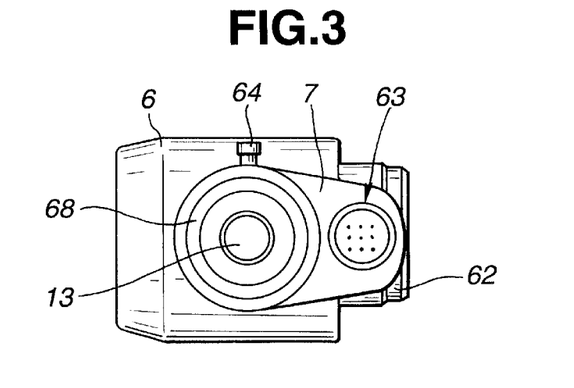
FIG. 3 is a cross-sectional detail view taken along lines III—III in FIG. 2.

As shown in FIG. 1, FIG. 2, and FIG. 3, the connector unit 6 has a light source connector 61, a video processor connector receptacle 62, and a magnification-control connector receptacle 63. The light source connector 61 juts out of one end surface of the connector unit 6 and is coupled to the light source apparatus 2, an external apparatus, so that the connector 61 can be uncoupled freely. The video processor connector receptacle 62 is a first electric connector receptacle to which a video connector 32 is coupled so that the video connector can be uncoupled freely. The video connector 32 is attached to one end of a video processor linkage cord 31 extending from the video processor 3. The magnification-control connector receptacle 63 is a second electric connector receptacle to which a control connector 42 is coupled so that the control connector can be uncoupled freely. The control connector 42 is attached to one end of a magnification control apparatus linkage cord 41 extending from the magnification control apparatus 4.

As shown in FIG. 2, formed on the sides of the connector unit 6 are a high-frequency terminal 64, an aeration/perfusion base 65, a suction base 66, and a gas base 67. The high-frequency terminal 64 conducts electricity to metallic members incorporated in the endoscope 1. The aeration/perfusion base 65 is connected to an aeration pump (not shown) and perfusion tank (not shown). The suction base 66 is connected to a suction pump (not shown). The gas base 67 is connected to a gas source for incombustible gas.

As illustrated, the video processor connector receptacle 62, high-frequency terminal 64, aeration/perfusion base 65, suction base 66, and gas base 67 are formed on the sides of the connector unit 6 and jut out orthogonally to the longitudinal direction of the light source connector 61.

The magnification control connector receptacle 63 is formed on an end surface opposite to the end surface from which the light source connector 61 projects. The magnification-control connector receptacle 63 is located so that the center axis thereof will be substantially parallel to the longitudinal axis of the light source connector 61.

The magnification-control connector receptacle 63 is located by the right-hand side of a magnification-control connector assembly 7. The magnification-control connector assembly 7 is interposed between the video processor connector receptacle 62 and an anti-breakage member 68.

The video processor connector receptacle 62 and magnification-control connector receptacle 63 are formed in the connector assembly 7 to foster smoothness in coupling or uncoupling. Specifically, the video processor connector receptacle 62 and the magnification-control connector receptacle 63 are located on the right-hand side with the connector unit opposed to the light source apparatus 2 (see FIG. 10).

The second electric connector receptacle is not limited to the magnification-control connector receptacle 63 but may be any electric connector receptacle to which a connector extending from the second control apparatus can be connected.

As shown in FIG. 3, the magnification-control connector assembly 7 is designed so as not to jut out beyond the contour of the connector unit 6 including the video processor connector receptacle 62.

Figure 4:
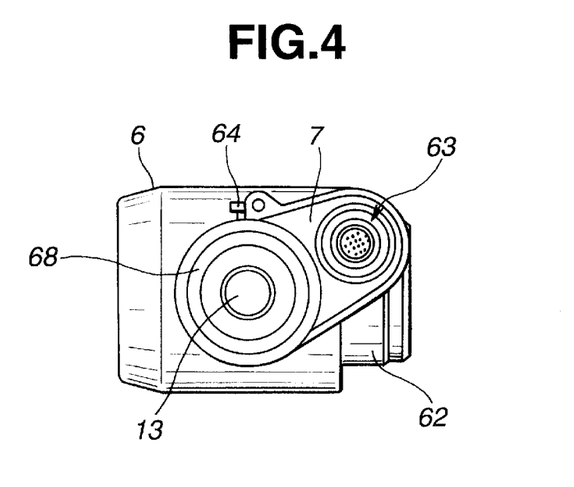
FIG. 4 is an alternative cross-sectional detail view taken along line III—III FIG. 2.

As shown in FIG. 4, the magnification-control connector assembly 7 may be disposed obliquely when the size of a connector receptacle increases because the number of pins associated with the electric connector increases.

A waterproof cap 69, shown in FIG. 1, is received on the magnification control connector receptacle 63. The waterproof cap 69 is bound to the magnification-control connector assembly 7 by a coupling member 70, such as a chain.

Figure 5:
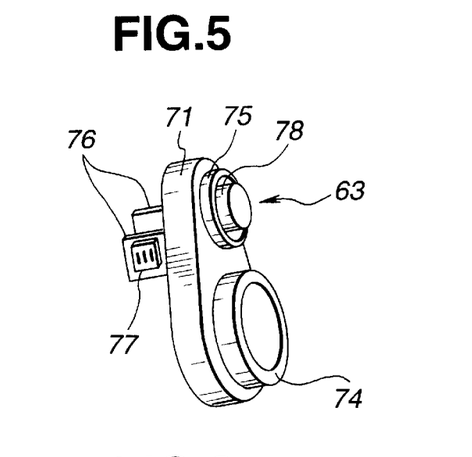
FIG. 5 is a top rear view of a connector body that is an integral part of the magnification-control connector unit of FIG. 1.
Figure 6:
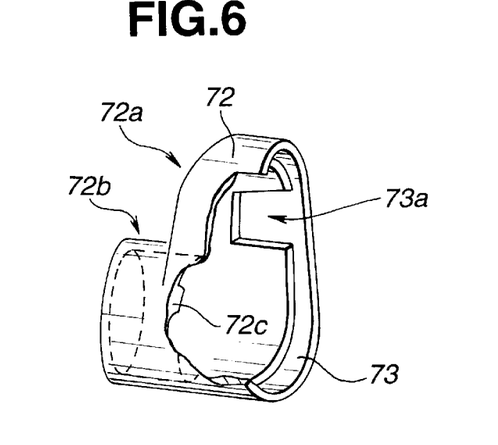
FIG. 6 is a partial top rear view for explaining a connector casing with a portion thereof cut away, that is an integral part of the magnification-control connector unit of FIG. 1.
Figure 7:
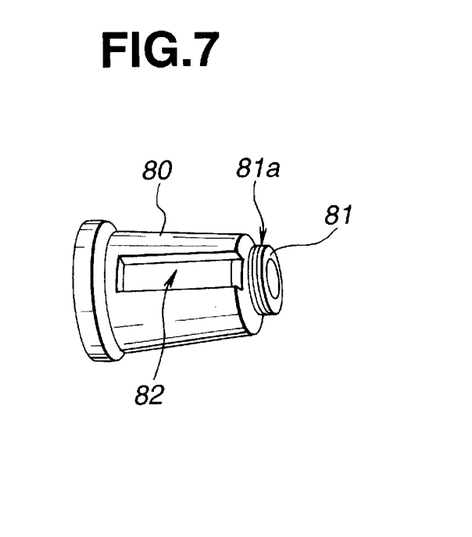
FIG. 7 is a perspective view of a coupling member for uniting the connector body and the connector casing.

Referring to FIG. 5 to FIG. 7, the magnification-control connector assembly 7 will be described below.

The magnification-control connector assembly 7 of FIG. 1 consists of the connector body 71 shown in FIG. 5 and a connector casing 72 shown in FIG. 6. The connector casing 72 has a body placement recess 73 in which the connector body 71 is locked. The connector body 71 and connector casing 72 are joined by a coupling member 80 shown in FIG. 7. The magnification-control connector assembly 7 is fixed at a predetermined position in the connector unit 6 as shown in FIG. 2.

The coupling member 80 shown in FIG. 7 is formed with a metallic member. The coupling member 80 is hollowed to have an internal space in which signal cables, tubes, and a light guide are inserted, and is shaped like a capped cone. An end surface of the tapered distal part has a convex part 81 having a through-hole communicating with the internal space. The convex part 81 is circumscribed with a male screw thread 81a. The male screw thread 81a engages with a female screw thread (not shown) formed in the lumen of the anti-breakage member 68. An engagement slit 82 communicating with the internal space is laterally formed on the outer circumference of the coupling member 80.

As shown in FIG. 5, two convex parts 74 and 75, each having a through-hole, are formed in one end surface of the connector body 71. Jutting out of the other end surface of the connector body 71 are, for example, two panels 76. A circuit for varying the rate at which the magnification is changed, and others are formed on the panels 76. A DIP switch 77, for changing magnification, is formed on the panels 76.

The pins of the DIP switch 77 face outwardly so that they can be manipulated easily.

The anti-breakage member 68 is received on the outer circumference of the convex part 74. The signal cables, tubes, and light guide are inserted into the through-hole of the convex part 74. A plurality of contact pins is inserted in the through-hole of the convex part 75. A body member 78 matched with the magnification-control connector receptacle 63 is placed in the through-hole of the convex part 75. This results in a coupling base to which the magnification-control connector receptacle 63 is coupled.

As shown in FIG. 6, the connector case 72 has a large-diameter portion 72a and a small-diameter portion 72b. The large-diameter portion 72a has the body placement recess 73, in which the connector body 71 is locked, formed therein. The small-diameter portion 72b provides a fitting hole whose that receives the outer circumference of the coupling member 80.

The depth of the body placement recess 73 is substantially the same as the thickness of the connector body 71. When the connector body 71 is locked in the body placement recess 73, the entrance-side end of the body placement recess 73 and one end of the connector body 71 are aligned.

A panel stowage indentation 73a, in which the panels 76 are stowed, is formed in the inner circumference of the body placement recess 73. An engagement boss 72c engageable with the engagement slit 82 is formed on the inner circumference of the fitting hole.

The jutting part of the large-diameter portion 72a bordering on the small-diameter portion has a curved surface so as to facilitate attachment of a tube to the suction base 66.

Figure 8:
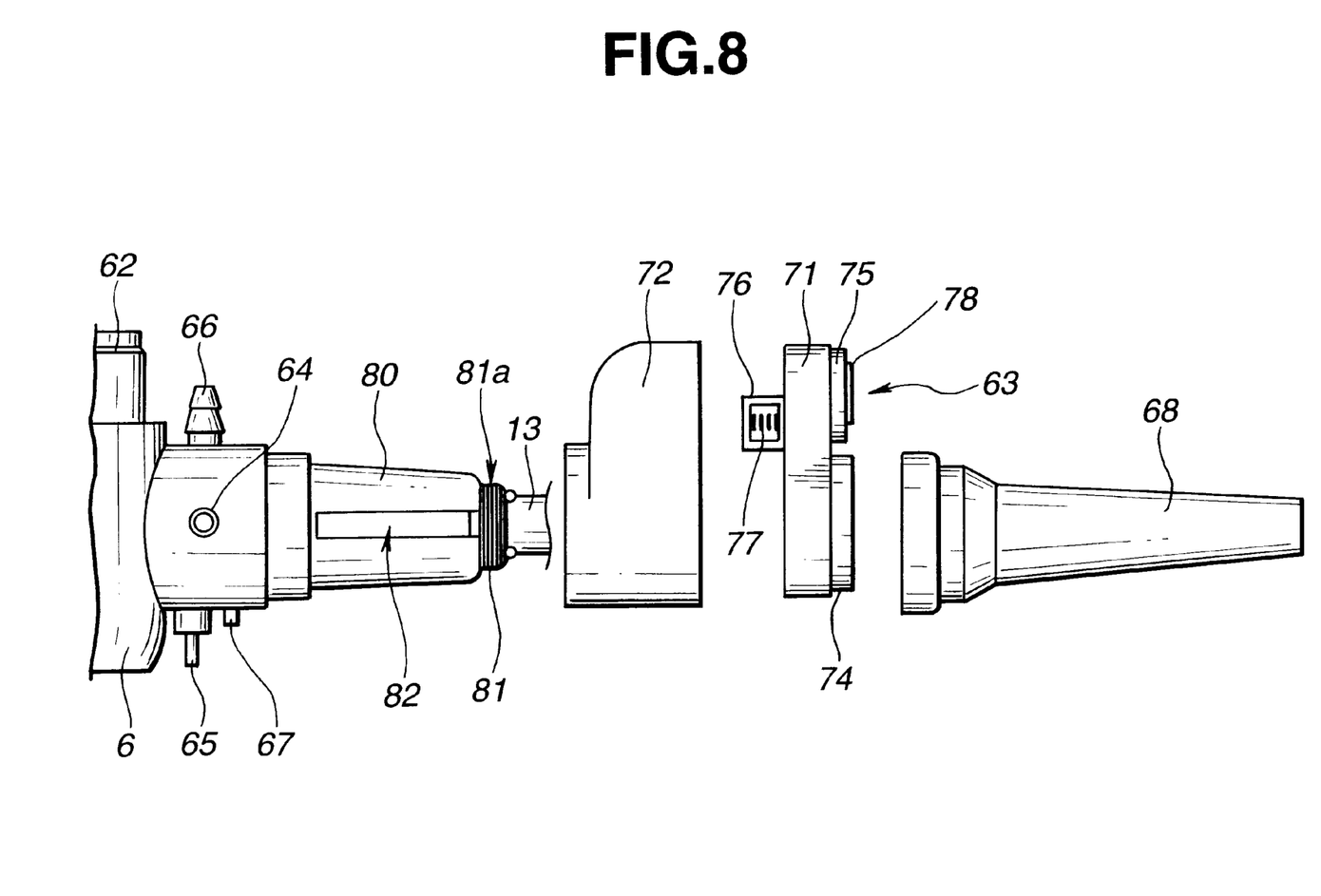
FIG. 8 is exploded side elevational view of the magnification-control connector unit of FIG. 1.

Referring to FIG. 8, a procedure of mounting the magnification-control connector assembly 7 on the connector unit 6, and the positional relationships among components will be described below.

To begin with, the coupling member 80 is placed at a predetermined position in the connector unit 6.

Thereafter, the connector body 71 is locked in the body placement recess 73 in the connector case 72. The magnification control connector assembly 7 is thus formed. At this time, the panels 76 jutting out of the connector body 71 are stowed in the panel-stowage, dentation 73a.

The magnification-control connector assembly 7 made by uniting the connector body 71 and connector case 72 with each other is mounted on the coupling member 80. At this time, the engagement boss 72c formed on the wall of the fitting hole of the small-diameter portion 72b of the connector case 72 is engaged with the engagement slit 82.

This restricts the rotation of the magnification-control connector assembly 7 relative to the coupling member 80. The magnification-control connector assembly 7 is located at a predetermined position. According to this embodiment, the magnification-control connector receptacle 63 is located on the right-hand side while facing the light source apparatus 2.

Finally, the anti-breakage member 68 is fitted on the convex part 74 of the connector body 71, and then rotated. This causes the female screw thread of the anti-breakage member 68 to engage with the male screw 81a threaded on the convex part 81 of the coupling member 80. The magnification-control connector assembly 7 is thus fixed to the connector unit 6.

Figure 9:
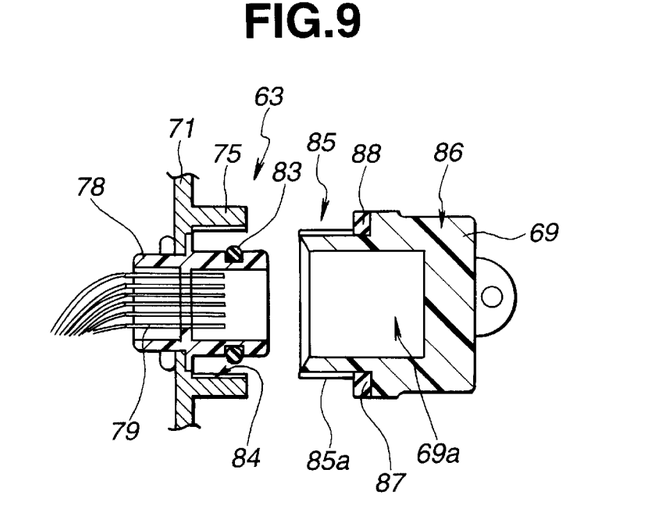
FIG. 9 is cross sectional detail view of the magnification-control connector unit and a watertight cap of FIG. 1.

Now, the relationship between the magnification control connector receptacle 73 and watertight cap 69 will be described with reference to FIG. 9.

The body member 78 shaped substantially like a pipe and provided with the plurality of contact pins 79 is inserted in the convex part 75 of the connector body 71. The body member 78 has a smaller diameter than the diameter of the lumen of the convex part 75. There is therefore a gap between the outer circumference of the body member 78 and the inner circumference of the convex part 75. The distal part of the watertight cap 69 is inserted in the gap.

A watertight rubber ring 83 having elasticity is received on the outer circumference of substantially the center part of the body member 78. A female screw thread 84 is threaded on the inner circumference of the convex part 75.

The watertight cap 69 that is substantially cylindrical has an internal space 69a defined by a wall is that is received on the outer circumference of the body member 78. The watertight cap 69 consists of a distal small-diameter portion 85 and a large-diameter portion 86. The distal small-diameter portion 85 is insert in the gap between the outer circumference of the body member 78 and the inner circumference of the convex part 75. The distal small-diameter portion 85 has a male screw thread 85a threaded on the outer circumference thereof. The large-diameter portion 86 is the back portion of the watertight cap 69 that communicates with the distal small-diameter portion 85. A watertight packing 88 is placed on an end surface of a stepped portion 87 between the large-diameter portion 86 and distal small-diameter portion 85.

The inner wall of the watertight cap 69 defining the internal space 69a is received on the outer circumference of the body member 78 provided with the contact pins 79. Consequently, the distal small-diameter portion 85 of the watertight cap 69 is inserted in the convex part 75 of the connector body 71.

In this state, the watertight cap 69 is rotated in a predetermined direction. This causes the male screw thread 85a threaded on the distal small-diameter portion 85 to engage with the female screw thread 84 threaded on the inner circumference of the convex part 75. The watertight cap 69 is thus advanced.

At this time, the watertight cap 69 is advanced while squeezing the watertight rubber ring 83 located on the body member 78 with the inner circumference of the distal small-diameter portion 85 thereof. The watertight cap 69 is further rotated and advanced. Mounting of the watertight cap 69 is thus completed. At this time, the watertight packing 88 on the stepped portion 87 of the watertight cap 69 comes into close contact with the top of the convex part 75 of the connector body 71.

When the watertight cap 69 is mounted on the magnification-control connector receptacle 63, the watertight rubber ring 83 on the body member 78 comes into close contact with the inner circumference of the distal small-diameter portion 85 while being squeezed. The watertight packing 88 put on the stepped portion 87 comes into close contact with the top of the convex part 75. This structure, the invasion of water from the magnification control connector receptacle 63 into the inside of the connector unit 6.

Operations to be performed by the endoscope system having the foregoing components will be described below.

Figure 10:
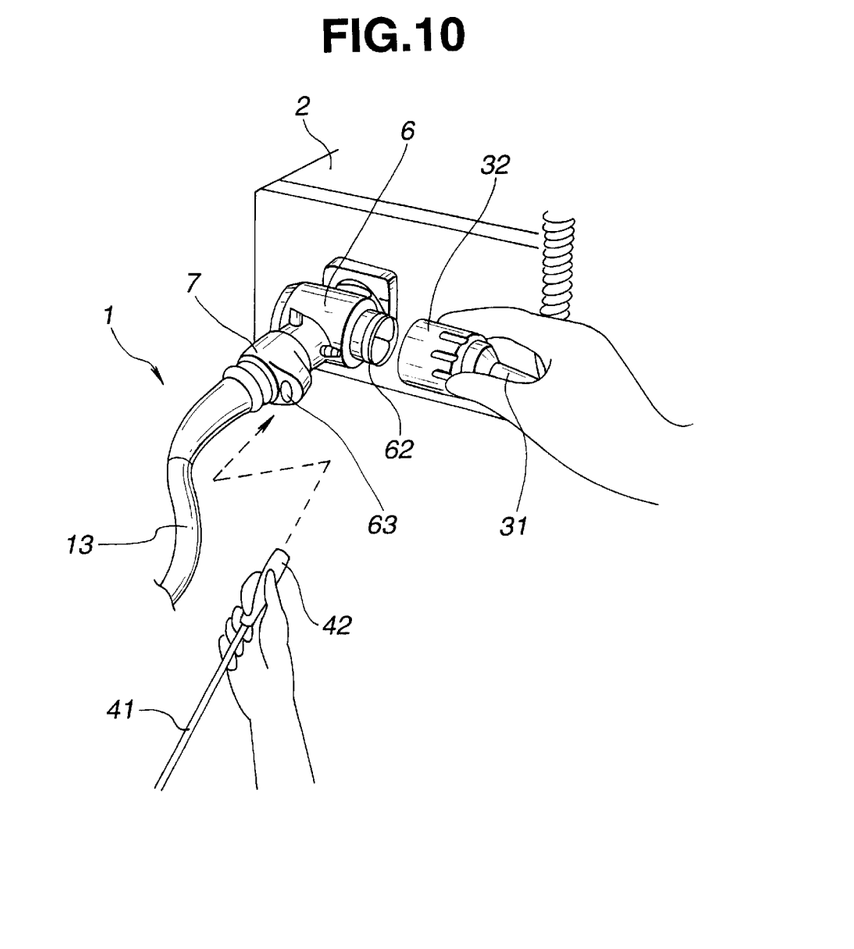
FIG. 10 is environmental perspective view of the connector unit coupled to a light source apparatus.

To begin with a user grasps, the operation unit 12 of the endoscope 1 with the user's left hand (not shown). Then the user grasps the connector unit 6 with the user's right hand. The light source connector 61 jutting from the connector unit 6 is inserted into a hole of the light source apparatus 2. Consequently, the connector unit 6 fixed to the proximal end of the universal cord 13 of the endoscope 1 is, as shown in FIG. 10, coupled to the light source apparatus 2.

Thereafter, the video connector 32 attached to the video processor linkage cord 31 extending from the video processor 3 in this coupled state is urged in a direction orthogonal to the direction in which the light source connector 61 is oriented when coupled to the light source apparatus 2. The video connector 32 is thus connected to the video processor connector receptacle 62. Consequently, the video connector 32 lies on the right-hand side of the connector unit 6 with the connector unit 6 opposed to the light source apparatus 2.

Thereafter, the control connector 42 attached to the magnification control apparatus linkage cord 41 extending from the magnification control apparatus 4 is urged in the same direction as the direction in which the light source connector 61 is oriented to be coupled to the light source apparatus 2. The control connector 42 is thus coupled to the magnification control connector receptacle 73 of the magnification-control connector assembly 7.

Consequently, the video processor linkage cord 31 lies in a direction orthogonal to the axis of the connector unit 6. The magnification control apparatus linkage cord 41 lies along the universal cord 13 extending from the connector unit 6.

Thereafter, electrodes and tubes are attached to or detached from the high-frequency terminal 64, aeration/perfusion base 65, suction base 66, and gas base 67 as required. At this time, the electrodes and tubes coupled to the high-frequency terminal 64, aeration/perfusion base 65, suction base 66, and gas base 67 extend in a direction orthogonal to the longitudinal direction of the connector unit 6.

As mentioned above, when a connector unit includes a plurality of electric connector receptacles, one electric connector receptacle is located on the right-hand side of the connector unit with the connector unit opposed to a light source apparatus. Another electric connector receptacle is located so that a connector will be oriented in the same direction as the direction in which a light source connector is oriented. The electric connector receptacle is located on the right-hand side of the connector unit. Consequently, the connectors attached to electric cables and mated with the electric connector receptacles are easily grabbed with the right hand and coupled to the electric connector receptacles. Smoothness in coupling the electric cables improves greatly because the electric cables are grabbed in a backhand manner.

One of the electric cables coupled to two electric connector receptacles extends in the same direction as the direction in which the light source connector is oriented, that is, extending along the universal cord direction. This reduces the congestion surrounding a connector. Cables, electrodes, and tubes are arranged neatly around the connector unit. Therefore, the smoothness in coupling the cables, electrodes, and tubes is greatly improved.

One electric connector receptacle is located so that the direction in which the electric connector receptacle receives an electric cable is the same as the direction in which a light source connector is inserted into a light source apparatus. For coupling the connector of the electric cable to the electric connector receptacle, the electric cable can be advanced toward the light source apparatus. The connector can therefore be smoothly coupled to the electric connector receptacle.

Figure 11:
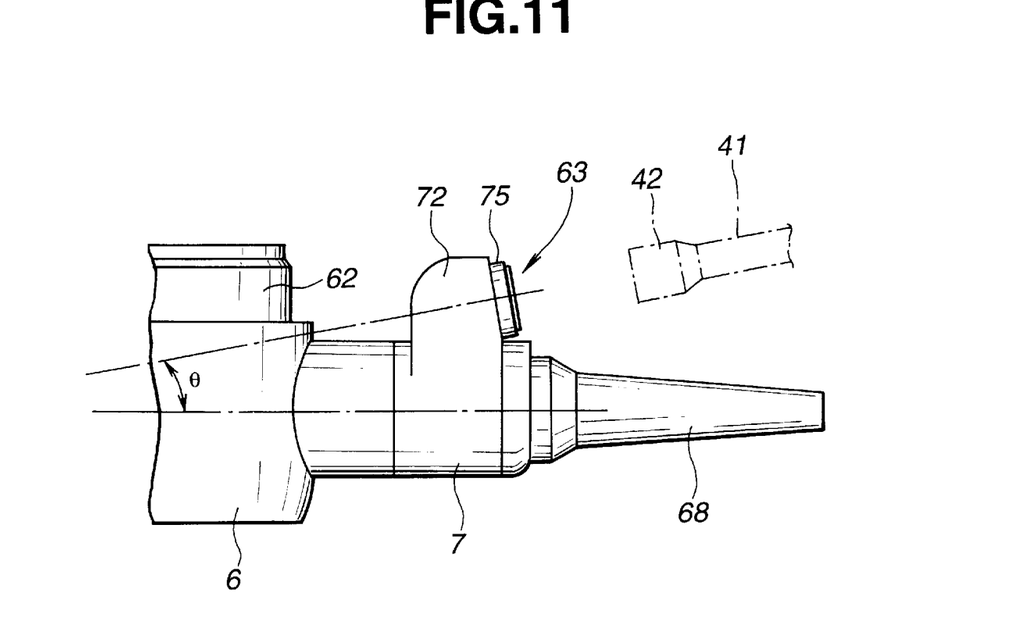
FIG. 11 is O side elevational view of another configuration of the magnification control connector included in the connector unit constructed according to principles of the invention.

As shown in FIG. 11, the center axis of the magnification-control connector receptacle 63 may be tilted at a predetermined angle θ in the range of 0° to 20° relative to the longitudinal axis of the connector unit 6. A large space can be preserved for coupling without any increase in the outer dimensions of the connector unit 6. At this time, the direction in which the magnification-control apparatus linkage cord 41 is oriented to be coupled to the magnification-control connector receptacle 63 is substantially the same as the direction in which the light source connector 61 is oriented to be coupled to the light source apparatus 2. The magnification control apparatus linkage cord 41 can be coupled easily and smoothly in the wide space provided.

Figure 12:
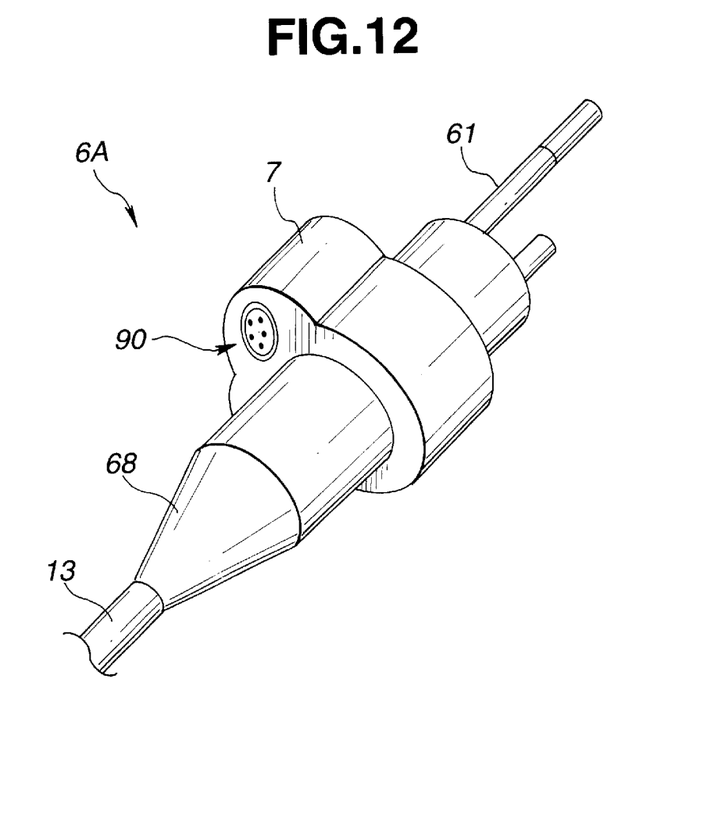
FIG. 12 is a top front view of another configuration of the connector unit constructed according to principles of the invention.

As shown in FIG. 12, when only one control apparatus (not shown) is included, a connector unit 6A may be attached to the proximal end of a universal cord that is one of the components of an optical endoscope. In this case, only one electric connector 90 is needed. The orientation of the electric connector 90 is therefore determined so that the direction in which an electric cable is inserted will be the same as the direction in which the light source connector 61 is oriented to be coupled to the light source apparatus 2. Consequently, the electric cable can be coupled to the light source apparatus smoothly. Moreover, since the surroundings of the connector unit are neatly straightened up, or uncongested the smoothness in coupling further improves. In consideration of the smoothness in coupling, the electric connector 90 should be located on the right-hand side of the connector unit 6A.

According to the present invention, it is apparent that a wide range of different embodiments can be constructed based on the invention without a departure from the spirit and scope of the invention. This invention will be limited by the appended claims but not restricted by any specific embodiments.

What is claimed is:

1. An endoscope system comprising:
    an endoscope;
    an operation unit attached to said endoscope;
    a connector unit fixed to the proximal end of a universal cord extending from said operation unit, the connector unit including a light source connector to be coupled to a light source apparatus and two electric connector receptacles;
    two control apparatuses for electrically controlling said endoscope;
    electric cables for electrically linking said control apparatuses and said endoscope; and connectors attached to said electric cables for being coupled to said electric connector receptacles,
    wherein, when the connector of one electric cable is fitted on a first electric connector receptacle of said two electric connector receptacles, the direction in which the connector is oriented to be fitted is orthogonal to the direction in which said light source connector is oriented to be coupled to said light source apparatus,
    wherein, when the connector of another electric cable is fitted on a second electric connector receptacle, the direction in which the connector is oriented to be fitted is the same as the direction in which said light source connector is oriented to be coupled to said light source apparatus,
    wherein said second electric connector receptacle is provided on a side of said connector unit relative to said light source connector so as to position said second electric connector closer to said operation unit than said first electric connector, and
    wherein said connector unit includes an anti-breakage member and a connector assembly which can be freely attached or detached between said first electric connector receptacle and said anti-breakage member, said second electric connector receptacle being provided in said connector assembly.

2. An endoscope system according to claim 1, wherein said connector assembly includes a connector body having said second electric connector receptacle formed therein, a connector casing having a body placement recess in which said connector body is locked, and a coupling member for joining said connector casing with said connector body.

3. An endoscope system according to claim 2, wherein said first electric connector receptacle and said second electric connector receptacle are located on one side of said connector unit with said connector unit being opposed to said light source apparatus.

4. An endoscope system according to claim 2, wherein said second electric connector receptacle is formed so that the center axis thereof is tilted at an angle ranging from 0° to 20° with respect to the longitudinal axis of said connector unit.

5. An endoscope system according to claim 4, further comprising a water-tight cap removably mountable on said second connector receptacle.

6. An endoscope system according to claim 1, further comprising a water-tight cap removably mountable on said second connector receptacle.

* * * * *